US009896471B2

(12) United States Patent
Baba et al.

(10) Patent No.: US 9,896,471 B2
(45) Date of Patent: Feb. 20, 2018

(54) SALT OF 1-(2-DEOXY-2-FLUORO-4-THIO-β-D-ARABINOFURANOSYL)CYTOSINE

(71) Applicant: FUJIFILM Corporation, Minato-ku, Tokyo (JP)

(72) Inventors: Yasutaka Baba, Toyama (JP); Tatsuya Murakami, Toyama (JP); Junko Shintani, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/498,334

(22) Filed: Sep. 26, 2014

(65) Prior Publication Data

US 2015/0011499 A1    Jan. 8, 2015

Related U.S. Application Data

(63) Continuation of application No. PCT/JP2013/058896, filed on Mar. 27, 2013.

(30) Foreign Application Priority Data

Mar. 28, 2012  (JP) .................................. 2012-074525
Mar. 13, 2013  (JP) .................................. 2013-050846

(51) Int. Cl.
| | |
|---|---|
| *C07H 19/06* | (2006.01) |
| *A61K 31/7068* | (2006.01) |
| *C07H 19/073* | (2006.01) |
| *C07C 309/66* | (2006.01) |
| *C07C 309/04* | (2006.01) |

(52) U.S. Cl.
CPC ......... *C07H 19/06* (2013.01); *A61K 31/7068* (2013.01); *C07C 309/04* (2013.01); *C07C 309/66* (2013.01); *C07H 19/073* (2013.01)

(58) Field of Classification Search
CPC ............................ C07H 19/06; A61K 31/7068
See application file for complete search history.

(56) References Cited

U.S. PATENT DOCUMENTS

| | | | |
|---|---|---|---|
| 3,116,282 A | 12/1963 | Hunter | |
| 3,243,425 A | 3/1966 | Whistler | |
| 4,211,773 A | 7/1980 | Lopez et al. | |
| 4,220,774 A | 9/1980 | Kuehne | |
| 4,803,272 A | 2/1989 | Anton et al. | |
| 5,811,408 A | 9/1998 | Yoshimura et al. | |
| 6,103,707 A | 8/2000 | Yamada et al. | |
| 6,147,058 A | 11/2000 | Yoshimura et al. | |
| 6,448,415 B1 | 9/2002 | Lee et al. | |
| 7,148,223 B2 | 12/2006 | Secrist, III et al. | |
| 7,285,572 B2 | 10/2007 | Shinagawa et al. | |
| 7,858,788 B2 | 12/2010 | Yoshida et al. | |
| 8,329,925 B2 | 12/2012 | Voigtlander et al. | |
| 8,420,831 B2 | 4/2013 | Voigtlander et al. | |
| 9,221,865 B2 | 12/2015 | Nakamura et al. | |
| 9,475,835 B2 | 10/2016 | Nakamura et al. | |

| | | | |
|---|---|---|---|
| 2003/0124054 A1 | 7/2003 | Toyohara et al. | |
| 2005/0129611 A1 | 6/2005 | Toyohara et al. | |
| 2006/0142238 A1 | 6/2006 | McGuigan | |
| 2009/0069263 A1 | 3/2009 | Damha et al. | |
| 2013/0252918 A1 | 9/2013 | McGuigan | |
| 2016/0355497 A1 | 12/2016 | Takeda et al. | |
| 2016/0355536 A1 | 12/2016 | Ito et al. | |
| 2016/0362389 A1 | 12/2016 | Nakamura et al. | |

FOREIGN PATENT DOCUMENTS

| | | |
|---|---|---|
| CN | 101058557 A | 10/2007 |
| CN | 101200463 A | 6/2008 |
| CN | 101880287 A | 11/2010 |
| EP | 0 841 344 A1 | 5/1998 |
| EP | 2 883 866 A1 | 6/2015 |
| JP | 53-119810 A | 10/1978 |
| JP | 55-49395 A | 4/1980 |
| JP | 56-92239 A | 7/1981 |
| JP | 5/178875 A | 7/1993 |
| JP | 6-501261 A | 2/1994 |
| JP | 8-53490 A | 2/1996 |
| JP | 8-504753 A | 5/1996 |
| JP | 10-282039 A | 10/1998 |
| JP | 2003-172990 A | 6/2003 |
| JP | 2005-503358 A | 2/2005 |
| JP | 2006-335737 A | 12/2006 |
| JP | 2006-528162 A | 12/2006 |
| JP | 2007-514643 A | 6/2007 |
| JP | 4202327 B2 | 12/2008 |
| JP | 2009-538829 A | 11/2009 |

(Continued)

OTHER PUBLICATIONS

Berge et al., J. Pharm. Sci., 1977, 66(1), p. 1-19.*
Serajuddin, A.T.M., Adv. Drug Deliv. Rev., 2007, 59(7), p. 603-616.*
JPO machine translation of JP 4202327 B2, JPO AIPN website, https://dossier1.j-platpat.inpit.go.jp/tri/all/odse/ODSE_GM101_Top.action, accessed online on Sep. 25, 2017. (Year: 2017).*
Office Action dated Mar. 19, 2015, issued by the Intellectual Property Office of Singapore in corresponding Singapore Application No. 11201406080V.
Office Action dated Jan. 28, 2015, issued by the Intellectual Property Office of New Zealand in corresponding New Zealand Application No. 701245.
Office Action mailed Apr. 7, 2015 in corresponding Japanese Application No. 2014-507938.
Office Action dated Aug. 21, 2015, issued by the Intellectual Property Office of New Zealand in corresponding New Zealand Application No. 701245.

(Continued)

*Primary Examiner* — Jonathan S Lau
(74) *Attorney, Agent, or Firm* — Sughrue Mion, PLLC (57) ABSTRACT

A superior antitumor agent is provided. A salt of 1-(2-deoxy-2-fluoro-4-thio-β-D-arabinofuranosyl)cytosine shows at least one or more of such characteristics as (1) it has superior antitumor activity, (2) it shows superior crystallinity, (3) it shows high water solubility, (4) it does not show deliquescent property, (5) it shows superior flowability, (6) it shows superior tableting property, (7) it can be manufactured with less environmental load, and (8) it can be manufactured in a large scale, and therefore it is useful as a bulk drug for medicaments.

10 Claims, 2 Drawing Sheets

(56) References Cited

FOREIGN PATENT DOCUMENTS

| | | |
|---|---|---|
| JP | 2010-59173 A | 3/2010 |
| JP | 4719356 B2 | 7/2011 |
| JP | 2011-526242 A | 10/2011 |
| JP | 2013-514260 A | 4/2013 |
| JP | 2013-146833 A1 | 10/2013 |
| JP | 2013-540129 A | 10/2013 |
| JP | 2014-027658 A1 | 2/2014 |
| WO | 91/04982 A1 | 4/1991 |
| WO | 94/05687 A1 | 3/1994 |
| WO | 96/01834 A1 | 1/1996 |
| WO | 97/37993 A1 | 10/1997 |
| WO | 97/38001 A1 | 10/1997 |
| WO | 97/49716 A1 | 12/1997 |
| WO | 99/28312 A2 | 6/1999 |
| WO | 99/43690 A1 | 9/1999 |
| WO | 02/058740 A1 | 8/2002 |
| WO | 03/000200 A2 | 1/2003 |
| WO | 2004/014930 A1 | 2/2004 |
| WO | 2004/014931 A1 | 2/2004 |
| WO | 2004/027658 A1 | 4/2004 |
| WO | 2004/100891 A2 | 11/2004 |
| WO | 2004/106352 A1 | 12/2004 |
| WO | 2005/012327 A2 | 2/2005 |
| WO | 2006/073197 A1 | 7/2006 |
| WO | 2007/068113 A1 | 6/2007 |
| WO | 2007/130783 A2 | 11/2007 |
| WO | 2011-074484 A1 | 6/2011 |
| WO | 2012/0455999 A2 | 4/2012 |
| WO | 2016/155593 A1 | 10/2016 |

OTHER PUBLICATIONS

Yuichi Yoshimura et al., "An Alternative Synthesis of Antineoplastic 4'-Thiocytidine Analogue 4'-ThioFAC", Pergamon, Tetrahedron Letters, 40, (1999), pp. 1937-1940.
Mayumi Takahashi et al., "Synthesis and crystal structure of 2'-deoxy-2'-fluoro-4'-thioribonucleosides: substrates for the synthesis of novel modified RNAs", Elsevier, Tetrahedron, 64, (2008), pp. 4313-4324.
Office Action dated Jul. 1, 2015 from the State Intellectual Property Office of the People's Republic of China in counterpart Chinese Application No. 201380016308.9.
Office Action (Patent Examination Report) dated Oct. 5, 2015, issued by the Australian Patent Office in counterpart Australian Application No. 2013241341.
Extended European Search Report (EESR) dated Oct. 12, 2015 from the European Patent Office in counterpart European Application No. 13770090.2.
Office Action dated Mar. 29, 2016, from the Canadian Intellectual Property Office in counterpart Canadian Application No. 2865742.
Office Action dated Mar. 21, 2016 in corresponding Russian Application No. 2014143277/04.
Office Action dated May 25, 2016 from the Taiwanese Intellectual Property Office in counterpart Taiwanese Application No. 102110915.
International Preliminary Report on Patentability, dated Oct. 9, 2014, from the International Bureau of WIPO in counterpart Application No. PCT/JP2013/058896.
Internal Preliminary Report on Patentability, dated Sep. 10, 2014, from the International Bureau of WIPO in International Application No. PCT/JP2013/058896.
Shinji Miura et al., "Comparison of 1-(2-deoxy-2-fluoro-4-thio-β-D-arabinofuranosyl)cytosine with gemcitabine in its antitumor activity", Cancer Letters 1999, pp. 177-182, vol. 144.
Yuichi Yoshimura et al., "An Alternative Synthesis of the Antineoplastic Nucleoside 4'-ThioFAC and Its Application to the Synthesis of 4'-ThioFAG and 4'-Thiocytarazid", J. Org. Chem. 1999, pp. 7912-7920, vol. 64.
Shinji Miura et al., "Potent antitumor effect of 1-(2-deoxy-2-fluoro-4-thio-β-D-arabinofuranosyl)cytosine on peritoneal dissemination models of gastrointestinal cancers", Oncology Reports 2002, pp. 1319-1322, vol. 9.

International Search Report for PCT/JP2013/058896 dated Jun. 4, 2013.
Office Action dated Nov. 5, 2015 from the Russian Patent Office in counterpart Russian Application No. 2014143277/04.
Office Action dated Oct. 25, 2016, issued by the Korean Intellectual Property Office in corresponding Korean Application No. 10-2014-7030209.
Office Action dated Sep. 13, 2016 from the Israeli Patent Office in counterpart Israeli Application No. 234222.
Office Action dated Sep. 30, 2016 from the Taiwanese Intellectual Property Office in counterpart Taiwanese Application No. 102110915.
Jeong, et al., The Stereochemical Outcome of the DAST Fluorination of 4'-Thipyrimidine Nucleosides with "Up" Hydroxyl Groups is Controlled by the Oxidation State of the Sulfur Atom, Chemistry Letters, pp. 301-302, 1995. (2 pages total).
Jeong, et al., Unanticipated Retention of Configuration in the DAST Fluorination of Deoxy-4'-thiopyrimidine Nucleosides with "Up" Hydroxyl Groups, Tetrahedron Letters, vol. 35, No. 41, pp. 7569-7572, 1994. (4 pages total).
Jeong, et al., Facile Fluorination of Deoxy-4'-thiopyrimidine Nucleosides with "Down" Hydroxyl Groups. Retention of Configuration After Fluoride Opening of the Quartenized $N^3$-MEM Anhydronucleosides, Tetrahedron Letters, vol. 35, No. 41, pp. 7573-7576,1994. (4 pages total).
Yoshimura, et al., Synthesis of 2'-deoxy-2'-fluoro-4'-thioarabinonucleosides as potential antitumor and antiviral agents from D-glucose, Nucleic Acids Symposium Series, No. 35, pp. 15-16, 1996. (2 pages total).
Yoshimura, et al., A Novel Synthesis of New Antineoplastic 2'-Deoxy-2'-substituted -4'-thiocytidines, Journal of Organic Chemistry, vol. 61, No. 3, pp. 822-823, 1996. (2 pages total).
Tann, et al., Fluorocarbohydrates in Synthesis. An Efficient Synthesis of 1-(2-Deoxy-2-fluoro-β-D-arabino-furanosyl)-5-iodouracil (β-FIAU) and 1-(2-Deoxy-2-fluoro-β-D-arabinofuranosyl) thymine (β-FMAU), Journal of Organic Chemistry, American Chemical Society, vol. 50, No. 19, 1985. pp. 3644-3647 (4 pages total).
Jeong, et al., Participation of sulfur occurred during the Mitsunobu reaction: synthesis of novel isodideoxythionucleosides, J. Chem. Soc., Perkin Trans. 1, pp. 3325-3326, 1998. (2 pages total).
Office Action dated May 12, 1999, which issued during the prosecution of U.S. Appl. No. 08/973,529 (now U.S. Pat. No. 6,147,058).
Office Action dated Apr. 26, 2017, issued from the Mexican Patent Office in counterpart Mexican Patent Application No. MX/a/2014/011182.
Office Action dated May 19, 2017, issued from the European Patent Office in counterpart European Patent Application No. 13770090.2.
International Preliminary Report on Patentability with a Translation of Written Opinion issued from the International Bureau in International Application No. PCT/JP2015/080885, dated May 11, 2017.
Notices of Allowance and Allowability dated Nov. 8, 1999, which issued during the prosecution of U.S. Appl. No. 08/973,529 (now U.S. Pat. No. 6,147,058).
Office Action dated Apr. 3, 2017 from the Korean Intellectual Property Office in counterpart Korean Application No. 10-2014-7030209.
Office Action in European Patent Application No. 13879640.4 dated May 8, 2017.
Giorgio Attardo et al, Efficient Synthesis of 5,8-Disubstituted-1,4-Dihydrobenzoxathiin-3-Oxides and Their Isomeric Structures, 4,7-Disubstituted-1,3-Dihydrobenzo[b] Thiophene-2,2-Dioxides, Tetrahedron Letters, vol. 35, No. 27, pp. 4743-4746, 1994.
William Plunkett et al., "Preclinical characteristics of gemcitabine", Anti-Cancer Drugs, 1995, pp. 7-13, vol. 6, Suppl. 6.
Larry W. Hertel et al., "Evaluation of the Antitumor Activity of Gemcitabine (2',2'-Difluoro-2'-deoxycytidine)", Cancer Research, Jul. 15, 1990, pp. 4417-4422, vol. 50.
Hayato Fujita et al., "Gene Expression Levels as Predictive Markers of Outcome in Pancreatic Cancer after Gemcitabine-Based Adjuvant Chemotherapy1,2", Neo Plasia, Oct. 2010, pp. 807-817, vol. 12, No. 10.

(56) References Cited

OTHER PUBLICATIONS

Magdalena Slusarczyk et al., "Application of ProTide Technology to Gemcitabine: A Successful Approach to Overcome the Key Cancer Resistance Mechanisms Leads to a New Agent (NUC-1031) in Clinical Development", J. Med. Chem, 2014, pp. 1531-1542, vol. 57, No. 4.
Hyunah Choo et al., "Synthesis, Anti-HIV Activity, and Molecular Mechanism of Drug Resistance of L-2',3'-Didehydro-2',3'-dideoxy-2'-fluoro-4'-thionucleosides", J. Med. Chem., 2003, pp. 389-398, vol. 46, No. 3.
A. G. Cottrell et al., "Reaction Of Sugar Chlorosulfates VII. Some Conformational Aspects", Canadian Journal of chemistry, Jul. 1, 1966, pp. 1483-1491, vol. 44, No. 13.
Johan Fanton e al., "Enzymatic and Organocatalyzed Asymmetric Aldolization Reactions for the Synthesis of Thiosugar Scaffolds", European Journal of Organic Chemistry, 2012, pp. 203-210.
International Preliminary Report on Patentability and Written Opinion of the international Searching Authority (forms PCT/IB388, PCT/373, PCT/ISA 237 and PCT/IB/326), dated Feb. 26, 2015, for International Application No. PCT/JP2013/071871.
International Search Report for PCT/JP2013/071871, dated Nov. 26, 2013.
Laetitia Jean-Baptise et al., "Synthesis of 2',3'-Dideoxy-2'-Fluoro-4'-Thionucleosides from a Fluoroxanthate", Synlett, 2008, pp. 817-820, No. 6.
Masajiro Kawana et al., "The Synthesis of 2',3'-Diodexycytidene and Its 2'-Azido Analogue Applications of the Deoxygenative [1,2]-Hydride Shift of Sulfonates with Mg(OMe)2-NaBH4", Chemistry Letters, 1987, pp. 2419-2422.
Naveen K. Khare et al., "Synthesis of 4-deoxy-4-thioarabinofuranosyl disaccharides, analogs of Mycobactrial arabinoglactan", Indian Journal of Chemistry, Nov. 2008, pp. 1748-1752, vol. 47B.
Office Action issued in U.S. Appl. No. 14/621,119, dated Mar. 24, 2015.
N. Otonani et al., "Preparation and Antitumor Activity of 4'-Thio Analogs of 2,2'-Anhydro-1-11-D-arabinofuranosylcytosine", Journal of Medicinal Chemistry, 1974, pp. 535-537, vol. 17, No. 5.
Wu-Bao Wang et al., "A Practical Synthesis of Sugar-Derived Cyclic Nitrones: Powerful Synthons for the Sysnthesis of Iminosugars", Synlett, 2010, pp. 488-482, No. 3.
Australian Office Action for Application No. 2013303534, dated Dec. 1, 2015.
Official Action for Canadian Patent Application No. 2,880,794, dated Nov. 2, 2015.
Chinese Office Action for Application No. 201280042642.1, dated Nov. 2, 2015.
Extended European Search Report for Application No. 13879640.4 dated May 18, 2016.
Japanese Office Action for Application No. 2014-563560 dated Mar. 1, 2016.
Korean Office Action for Application No. 10-2015-7003655, dated May 12, 2016.
Office Action issued in U.S. Appl. No. 14/873,966, dated Feb. 8, 2016.
Notice of Allowance issued in U.S. Appl. No. 14/873,966, dated May 26, 2016.
Partial Supplementary European Search Report issued in European Application No. 13879640.4, dated Feb. 16, 2016.
Supplemental Notice of Allowance issued in U.S. Appl. No. 14/873,966, dated Jul. 6, 2016.
Russian Office Action for Application No. 2015108790, dated Apr. 25, 2016.
Kamal N. Tiwari et al., "Synthesis and Biological Activity of 4'-Thio-Lxylofuranosyl Nuclesides", Nucleosides, Nucleotides & Nucleic Acids, 2001, pp. 743-746, vol. 20, Nos. 4-7.
Yuichi Yoshimura et al., "Synthetic Studies on 2'-Substituted-4'-Thiocytidine Derivatives As Antineoplastic Agents", Nucleosides & Nucleotides, 1999, pp. 815-820, vol. 18, Nos. 4 & 5.
Official Action issued in the Canadian Patent Application No. 2,880,794, dated Aug. 18, 2016.
Notice of Final Rejection issued in Korean Patent Application No. 10-2015-7003655, dated Nov. 21, 2016.
Official Action issued in Korean Patent Application No. 10-2015-7003655, dated Jan. 11, 2017.
Feng Zheng et al., "Synthesis of L-13-3'Deoxy -2',3'-difluoro-4'-thionucleosides", Organic Letters, 2006, pp. 6083-6086, vol. 8, No. 26.
Takashi Komine et al., "Synthesis and Structure-Activity Relationship Studies of Highly Potent Novel Oxzolidinone Antibacterials", J. Med. Chem., vol. 51, No. 20, pp. 6558-6562, 2008.
Shinji Miura et al., "Antitumor activity of a novel orally effective nucleoside, 1-(2-deoxy-2-fluoro-4-thio-B-D-arabinofuranosyl) cytosine", Cancer Letters, 1998, pp. 103-110, vol. 129.
Koen Vanhessche et al., "L-Ribulose A: Novel Chiral Pool Compound", Tetrahedron Letters, pp. 2337-2340, 1990, vol. 31, No. 16.
Oscar Varela et al., "First Synthesis of Aldopentono-1,4-thiolactones", J. Org. Chem., 1993, pp. 7860-7864, vol. 58, No. 27.
Chia-Lin J. Wang et al., "Synthesis of 2'(S), 3'(R), 5'-Trihydroxypentyladeninei", Tetrahedron Letters, 1988, pp. 1107-1110, vol. 29, No. 10.
Jonathan K. Watts et al., Synthesis and Conformal Analysis of 2'-Fluoro-5-methyl-4'-thioarabinouridine (4'S-Famau), J. Org. Chem., 2006, pp. 921-924, vol. 71.
Yuichi Yoshimura et al., "A Novel Synthesis of 2'-Modified 2'-Deoxy-4'-thocytidines from D-Glucosel", J. Org. Chem., 1997, pp. 3140-3152, vol. 62, No. 10.
Yuichi Yoshimura et al., "An alternative synthesis of antineoplastic nucleoside 4'-thioFAC", nucleic Acids Symposium Series, 1998, pp. 11-12, No. 39.
Yuichi Yoshimura e al., "Synthesis and Biological Activities of 2'-Deoxy-2'fluoro-4'thioarabinofuranosylpyrimidine and -Purine Nucleosides", Bioorganic & Medicinal Chemistry, 2000, pp. 1545-1558, vol. 8.
Deborah A. Zajchowski et al., "Anti-tumor efficacy of the nucleoside analog 1-(-deoxy-2-fluoro-4-thio-B-D-arabinofuranosyl) cytosine (4'-thio-Fac) on human pancreatic and ovarian tumor xenograft models", Int. J. Cancer, 2005, pp. 1002-1009, vol. 114.
Partial European Search Report issued in European Patent Application No. 10163406.1, dated Nov. 24, 2010.
PCT International Preliminary Report on Patentability (IPRP), dated Jun. 28, 2012 for PCT International Application No. PCT/JP2010/072182.
International Search Report and Written Opinion for PCT/JP2010/072182, dated Apr. 29, 2011.
Thomas B. Mercer et al., Looking glass inhibitors: both enantiomeric N-benzyl derivatives of 1,4-dideoxy-1,4-imino-D-lyxitol [a potent competitive inhibitor of a-D-glactosidase ] and of 1-4- dideoxy-1,4-imino-L-lyxitol [a weak competitive inhibitor of a-D-glactosidase] inhibit naringinase, an a-L-rhamnosidase competitively, Tetrahedron: Asymmetry, 2009, pp. 2368-2373, vol. 20, No. 20.
Paul Karrer, "Organic Chemistry", 2nd English Edition, Elsevier Publ. Comp., Inc. NY, pp. 92-102.
International Search Report for PCT/JP2015/080885, dated Feb. 2, 2016.
Written Opinion for PCT/JP2015/080885, dated Feb. 2, 2016.
Official Action issued in Russian Patent Application No. 2015108790, dated Dec. 29, 2016.
Extended European Search Report issued in European Patent Application No. 17150141.4, dated Mar. 16, 2017.
Official Action issued in Chinese Patent Application No. 201380042642.1, dated Jan. 16, 2017.
David Baker et al., "Large-scale preparation of D-allose: observations on the stereoselectivity of the reduction of 1,2:5,6-di-O-isopropylidene-a-D-ribo-hexofuranos-3-ulose hydrate", Carbohydrate Research, 1972, pp. 192-197, vol. 24.

(56) References Cited

OTHER PUBLICATIONS

Lak Shin Jeong et al., "N[6]-Substituted D-4'-Thioadenosine-5'-methyluronamides: Potent and Selective Agonists at the Human A3 Adenosine Receptor", J. Med. Chem., 2003, pp. 3775-3777, vol. 46, No. 18.
Jeong et al., Chemistry Letters, pp. 301-302, 1995.
Jeong et al., Tetrahedron Letters, 35(41):7569-7572, 1994.
Jeong et al., Tetrahedron Letters, 35(41):7573-7576, 1994.
Y. Yoshimura et al., Nucleic Acids Symposium Series, No. 35, pp. 15-16 (1996).
Y. Yoshimura et al., Journal of Organic Chemistry, vol. 61, No. 3, pp. 822-823 (1996).
Office Action dated Nov. 8, 2012 in U.S. Appl. No. 13/606,746 (now U.S. Pat. No. 8,420,831).
Notice of Allowance dated Aug. 30, 2012 in U.S. Appl. No. 12/959,735 (now U.S. Pat. No. 8,329,925).
Office Action dated May 19, 2017, issued from the Canadian Patent Office in corresponding Canadian Patent Application No. 2,880,794.
Zheng, F., et al., "*Synthesis of L-β-31-Deoxy-3,3'-difluoro-41-thionucleosides*", Organic Letters, vol. 8, No. 26, pp. 6083-6086, 2006 (4 pages total).
Communication dated Apr. 4, 2017 from the Japanese Patent Office in Japanese Application No. 2014- 029978.
Communication dated Mar. 28, 2017 from the European Patent Office in European Application No. 15751531.3.
Communication dated Mar. 13, 2017 from the U.S. Appl. No. 15/238,232.
Communication dated Apr. 18, 2017 from the Japanese Patent Office in Japanese Application No. 2016- 504110.
Communication dated Jan. 31, 2017 from the European Patent Office in European Application No. 15751503.2.
Communication dated Jul. 2, 2015 from the U.S. Patent and Trademark Office in Application No. 14/621,119.
Communication dated Nov. 30, 2015 from the U.S. Appl. No. 14/621,119.
Communication dated Sep. 12, 2016 from the U.S. Appl. No. 14/873,966.
Vorbruggen et al., Org. Reactions (2000), pp. 55.
Watts et al., Nuclei. Acids Res. (2007) vol. 35(5), pp. 1441-1451.
Karrer, Org Chem. 2nd Ed. (1996). pp. 92-102.
Kamal N. Tiwari et al., "The Synthesis and Biological Activity of 1-(2-Deoxy-4-Thio-a-L-Threo-Pentofuranosyl) Thymine", Nucleosides & Nucleotides, 12(8), pp. 841-846 (1993).
Hiroshi Satoh et al., "Synthesis of L-Enantiomers of 4'-Thioarabinofuranosyl Pyrimidine Nucleosides", Bioorganic & Medicinal Chemistry Letters 8 (1998) pp. 989-992.
Yuichi Yoshimura et al., "A Facile, Alternative Synthesis of 4'-Thioarabinonucleosides and their Biological Activities", J. Med. Chem. 1997, 40(14); pp. 2177-2183.
Yun-Lung Fu et al., "An Alternative Synthesis of Anorneric Methyl 2-Deoxy-4-thio-D-erythro-pentofuranosides", J. Org. Chem., vol. 41, No. 24; 1976, pp. 3831-3834 (4 pages total).
John A. Secrist III et al., "Synthesis and Biological Activity of 2'-Deoxy-4'-thio Pryimidine Nucleosides", J. Med. Chem. 1991, 34, No. 8 (pp. 2361-2366).
International Search Report, issued by International Searching Authority on May 19, 2015, in International Application No. PCT/JP2015/054305.
Martin W. Bredenkamp et al., "Stannylene Directed Selective Acylation of Some Open-Chain L-Arabinose Derivatives", Tetrahedron Letters, 1990, 31(19) pp. 2759-2762.
Elmer J. Reist et al., "Thio Sugars, Synthesis of the Adenine Nucleosides of 4-Thio-D-Xylose and 4-Thio-D-Arabinose", Journal of Organic Chemistry, 1968, 33(1) pp. 189-192.
Elmer J. Reist et al., "Synthesis the 4 Thio D and L Ribofuranose and the Corresponding Adenine Nucleosides", Journal of the American Chemical Society, 1964, 86(24), pp. 5658-5663.
Stephanie A. Hartsel et al., "Synthesis of 9-(4-Thioxylofuranosyl) adenine via a Novel Glycosylation Reaction", Tetrahedron Letters 39 (1998) pp. 205-208.

Vjera Pejanovic et al., "Synthesis and Biological Evaluation of Some Novel 4'-Thio-L-ribonucleosides with Modified Nucleobase Moieties", Bioorganic & Medicinal Chemistry Letters, 2003, 13(11) pp. 1849-1852.
Kamal N. Tiwari et al., "Synthesis and Anti-cancer Activity of Some Novel 5-Azacytosine Nucleosides", Nucleosides, Nucleotides & Nucleic Acids, 2003, 22(12), pp. 2161-2170.
International Preliminary Report on Patentability issued from the International Bureau in International Application No. PCT/JP2015/054305, dated Jan. 4, 2016.
Peter Haeberli et al., "Syntheses of 4'-thioribonucleosides and thermodynamic stability and crystal structure of RNA oligomers with incorporated 4'-thiocytosine", Nucleic Acids Research, 2005, vol. 33, No. 13; pp. 3965-3975.
G. Inguaggiato et al., "Novel Triazole 2'-Deoxy-4'-Thionucleosides: Stereoselective Synthesis and Biological Evaluation", Nucleosides & Nucleotides, 1999; vol. 18 No. 3; pp. 457-467.
Houssine Ait-sir et al., "Synthesis and configurational assignments of 3-substituted 2-deoxy-4-thio-D-erythro-pentofuranose derivatives", Journal of the Chemical Society, Perkin transactions 1, 1996; No. 14; pp. 1665-1671.
Miura et al., "Suppression of Peritoneal Dissemination by 4'-thio-FAC," Oncology Reports, vol. 9, No. 6, Nov.-Dec. 2002, pp. 1319-1322 (9 pages total).
King, "Bioisosteres, Conformational Restriction, and Pro-drugs—Case History: An Example of a Conformational Restriction Approach," Med. Chem., Principle and Practice (1994), pp. 206-208.
Communication dated Dec. 22, 2016, from the European Patent Office in European Application No. 15751531.3.
Cox, J.M., et al., "Cyclic Hemithioacetals: Analogues of Thiosugars with Sulphur in the Ring", J. Chem. Soc., Section C, 1967, pp. 1130-1134.
International Search Report, issued by International Searching Authority in International Application No. PCT/JP2015/052304, dated Mar. 10, 2015.
Hua Lin et al., "Highly Efficient Asymmetric Synthesis of Enantipure Dihydro-1, 2-oxazines: Dual-Organocatalyst-Promoted Asymmetric Cascade Reaction", Organic Letters (2012), vol. 14, No. 15; pp. 3818-3821.
David A. Berges et al., "Bicyclic diazasugars. Part 3: B-D-Mannose and 6-deoxy-8-L-gulose analogues", Tetrahedron, 2001, vol. 57; pp. 9915-9924.
Ronald C. Horton Jr. et al, "Aldehyde-Terminated Self-Assembled Monolayers on Gold: Immobilization of Amines onto Gold Surfaces", J. Am. Chem. Soc., 1997, vol. 119; pp. 12980-12981.
H. Driguez et al., "A Novel Synthesis of 5-Thio-D-Glucose" Tetrahedron Letters, 1981, vol. 22, No. 50, pp. 5061-5062.
R. M. Rowell et al., "Derivatives of a-D-Glucothiopyranose", J. Org. Chem., 1996, vol. 31; pp. 1514-1516.
Eva Bozo et al., "Synthesis of 4-cyanophenyl and 4-nitrophenyl 1,5-dithio-L-and -D- arabinopyranosides possessing antithrombotic activity1,2", Carbohydrate Research 1998, vol. 311; pp. 191-202.
International Preliminary Report on Patentability issued from the International Bureau in International Application No. PCT/JP2015/052304, dated Feb. 16, 2016.
Johan Fanton et al., "Enzymatic and Organocatalyzed Asymmetric Aldolization Reactions for the Synthesis of Thiosugar Scaffolds", Eur. Journal Org. Chem. 2012, pp. 203-210.
Junji Fujita et al., "Synthesis of thiosaccharides employing the Pummerer rearrangement of tetrahydrothiopyran oxides", Tetrahedron 2004, vol. 60, No. 32, pp. 6829-6851.
Dusan Miljkovic et al., "An improved synthesis of methyl 5-thio-D-arabino-pyranosides", Journal of the Serbian Chemical Society, vol. 55, 1990; pp. 359-361.
Hironobu Hashimoto et al., "Novel conversion of aldopyranosides into 5-thioaldopyranosides via acyclic monothioacetals with inversion and retention of configuration at C-5", Carbohydrate Research, vol. 282, Issue 2 (Feb. 23, 1996) pp. 207-221.
Communication dated Jun. 14, 2017 from the State of Israel Patent Office in Israeli Application No. 237086.
Office Action dated Jun. 23, 2017, in co-pending U.S. Appl. No. 15/581,834.

(56) References Cited

OTHER PUBLICATIONS

Joseph V. Simone, Part XIV, Oncology: Introduction, Cecil Textbook of Medicine, 20th Edition, vol. 1, 1995, pp. 1004-1010 (8 pages total).
Homer L. Pearce et al., "Failure modes in anticancer drug discovery and development", Cancer Drug Design and Discovery, edited by Stephen Neidle, Chapter 18, 2008 (pp. 424-435).
Jl Johnson et al., "Relationships between drug activity in NCI preclinical in vitro and in vivo models and early clinical trials", British Journal of Cancer, 84 (10), 2001 (pp. 1424-1431).
Trisha Gura et al., "Cancer Models: Systems for Identifying New Drugs Are Often Faulty", Science, vol. 278, No. 5340, pp. 1041-1431, Nov. 7, 1997 (5 pages total).
Office Action dated Mar. 13, 2017, in co-pending U.S. Appl. No. 15/238,784.
Communication dated Mar. 1, 2016, from the Japanese Patent Office in counterpart application No. 2014-530560.
Office Action in Taiwanese Application No. 099142198 dated Sep. 11, 2014.
Office Action issued in Australian Application No. 2010331367 dated Jul. 25, 2016.
Office Action issued in Canadian Application No. 2,784,399 dated Oct. 6, 2016.
Office Action issued in European Application No. 10801279.0 dated Jun. 4, 2013.
Office Action issued in European Application No. 10801279.0 dated Dec. 16, 2013.
Extended European Search Report (EESR) issued in European Application No. 14177042.0 dated Oct. 2, 2014.
Office Action issued in European Application No. 14177042.0 dated Aug. 19, 2015.
Office Action issued in Korean Application No. 10-2012-7018741 dated Dec. 1, 2016.
Office Action issued in Russian Application No. 2012130422 dated Jan. 22, 2015.
Office Action issued in Singapore Application No. 2012044368 dated Jun. 11, 2014.
Office Action issued in Vietnamese Application No. 1-2012-02041 dated Jul. 4, 2013.
Office Action issued in Vietnamese Application No. 1-2012-02041 dated Mar. 7, 2014.
Office Action issued in Chinese Application No. 201380042642.1 dated Aug. 2, 2017.
Extended European Search Report (EESR) issued in European Application No. 15853887.6 dated Aug. 17, 2017.
J. Allen Miller et al., "2,2'-Anhydro-4'-Thionucleosides: Precursors for 2'-Azido- and 2'-Chloro-4'-thionucleosides and for a Novel Thiolane to Thietane Rearrangement", Nucleosides, Nucleotides and Nucleic Acids, vol. 19, No. 9, 24 Sep. 2000, pp. 1475-1486, XP055207502.
Raoul, S., et al., "$^1$H, $^{13}$C and $^{15}$N Nuclear magnetic resonance analysis and chemical features of the two main radical oxidation products of 2'-deoxyguanosine: oxazolone and imidazolone nucleosides", J. Chemical Soc., Perkin Trans. 2, 1996, Issue 3, pp. 371-381 (11 pages).
Office Action dated Sep. 26, 2017 from the Japanese Patent Office in Japanese Application No. 2016-136575.
PCT International Preliminary Report on Patentability (IPRP), dated Jun. 19, 2012 for PCT International Application No. PCT/JP2010/072182.
Office Action dated Oct. 27, 2017, from Intellectual Property India in Indian Patent Application No. 6251/CHENP/2012.

\* cited by examiner

SALT OF 1-(2-DEOXY-2-FLUORO-4-THIO-β-D-ARABINOFURANOSYL)CYTOSINE

CROSS REFERENCE OF THE RELATED APPLICATIONS

This application claims the convention priority based on Japanese Patent Application No. 2012-074525 filed on Mar. 28, 2012 at the Japanese Patent Office, and Japanese Patent Application No. 2013-050846 filed on Mar. 13, 2013 at the Japanese Patent Office. The entire disclosures of these applications are incorporated into the disclosure of the present application.

TECHNICAL FIELD

The present invention relates to a salt of 1-(2-deoxy-2-fluoro-β-D-arabinofuranosyl)cytosine, which is useful as an antitumor agent.

BACKGROUND ART

It is known that 1-(2-deoxy-2-fluoro-4-thio-β-D-arabinofuranosyl)cytosine (henceforth also referred to as "Compound A") has superior antitumor activity, and is useful as a therapeutic agent for tumors (Patent document 1). It is also known that Compound A shows potent antitumor activity even when it is orally administered to mice (Non-patent documents 1 and 2).

PRIOR ART REFERENCES

Patent Document

Patent document 1: International Patent Publication WO97/038001

Non-Patent Documents

Non-patent document 1: Cancer Letters, Vol. 144, pp. 177-182, 1999
Non-patent document 2: Oncology Reports, Vol. 9, pp. 1319-1322, 2002

SUMMARY OF THE INVENTION

Object to be Achieved by the Invention

Compound A suffers from low water solubility, and therefore it is necessary to improve the solubility for use as a medicament for humans. Compound A also suffers from poor flowability and tableting property, and therefore it has a problem concerning pharmaceutical manufacturing using it.

Thus, there is highly desired Compound A showing high water solubility, superior storage stability, flowability, and/or tableting property.

Means for Achieving the Object

The inventors of the present invention conducted various researches under such a situation as mentioned above. As a result, they found that a salt of Compound A has at least one or more of such characteristics as (1) it has superior antitumor activity, (2) it shows superior crystallinity, (3) it shows high water solubility, (4) it does not show deliquescent property, (5) it shows superior flowability, (6) it shows superior tableting property, (7) it can be manufactured with less environmental load, and (8) it can be manufactured in a large scale, and therefore it is useful as a bulk drug for medicaments, and thus they accomplished the present invention.

The present invention provides the followings.

[1] A pharmaceutically acceptable salt of 1-(2-deoxy-2-fluoro-4-thio-β-D-arabinofuranosyl)cytosine.
[2] The salt according to [1], which is a mineral acid salt or a sulfonate.
[3] The salt according to [2], wherein the mineral acid salt is hydrochloride, hydrobromide, hydroiodide, nitrate, phosphate, or sulfate; and the sulfonate is methanesulfonate, benzenesulfonate, p-toluenesulfonate, mesitylenesulfonate, or naphthalenesulfonate.
[4] The salt according to [2], wherein the mineral acid salt is hydrochloride, hydroiodide, nitrate, or sulfate; and the sulfonate is methanesulfonate.
[5] The salt according to [2], wherein the mineral acid salt is hydrochloride; and the sulfonate is methanesulfonate.
[6] A crystal of methanesulfonate of 1-(2-deoxy-2-fluoro-4-thio-β-D-arabinofuranosyl)cytosine showing characteristic peaks at diffraction angles (2θ) of 19.8, 21.8, 27.5, 28.4, and 29.9 degrees in powder X-ray diffractometry, or a crystal of hydrochloride of 1-(2-deoxy-2-fluoro-4-thio-β-D-arabinofuranosyl)cytosine showing characteristic peaks at diffraction angles (2θ) of 9.2, 14.7, 15.7, 22.9, and 27.3 degrees in powder X-ray diffractometry.
[7] A pharmaceutical composition containing the salt according to any one of [1] to [5], or the crystal according to [6].
[8] The pharmaceutical composition according to [7], which is for use in a treatment of a tumor.
[9] A method for preparing the salt according to any one of [1] to [5], which comprises the step of converting 1-(2-deoxy-2-fluoro-4-thio-β-D-arabinofuranosyl)cytosine into a pharmaceutically acceptable salt thereof.

The present invention further provides the followings.

A salt of 1-(2-deoxy-2-fluoro-4-thio-β-D-arabinofuranosyl)cytosine having an antitumor activity.

Use of a salt of 1-(2-deoxy-2-fluoro-4-thio-β-D-arabinofuranosyl)cytosine for manufacture of an antitumor agent or manufacture of a medicament for use in a treatment of a tumor.

A method for a treatment of a tumor, which comprises the step of administrating a salt of 1-(2-deoxy-2-fluoro-4-thio-β-D-arabinofuranosyl)cytosine to an object.

A salt of 1-(2-deoxy-2-fluoro-4-thio-β-D-arabinofuranosyl)cytosine for use in a method for a treatment of a tumor.

Effect of the Invention

The salt of the present invention has at least one or more of such characteristics as (1) it has superior antitumor activity, (2) it shows superior crystallinity, (3) it shows high water solubility, (4) it does not show deliquescent property, (5) it shows superior flowability, (6) it shows superior tableting property, (7) it can be manufactured with less environmental load, and (8) it can be manufactured in a large scale, and therefore it is useful as a bulk drug for medicaments.

The salt of the present invention shows, in particular, superior water solubility.

The salt of the present invention does not show deliquescent property, and shows, in particular, superior storage stability.

MODES FOR CARRYING OUT THE INVENTION

Hereafter, the present invention will be explained in detail. In the present invention, the values accompanied by "%" are used on the mass basis, unless specifically indicated, and the ranges indicated with "-" are ranges including the values on both sides of "-", unless specifically indicated.

The present invention provides a pharmaceutically acceptable salt of Compound A. Examples of the pharmaceutically acceptable salt include a mineral acid salt, an organic carboxylate, and a sulfonate. Preferred examples of the salt include a mineral acid salt and a sulfonate.

Examples of the mineral acid salt include, for example, hydrochloride, hydrobromide, hydroiodide, nitrate, phosphate, and sulfate, hydrochloride, hydroiodide, nitrate, and sulfate are preferred, and hydrochloride is more preferred. Examples of the organic carboxylate include, for example, formate, acetate, citrate, oxalate, fumarate, maleate, succinate, malate, tartrate, aspartate, trichloroacetate, and trifluoroacetate. Examples of the sulfonate include, for example, methanesulfonate, benzenesulfonate, p-toluenesulfonate, mesitylenesulfonate, and naphthalenesulfonate, and methanesulfonate is preferred.

The salt of the present invention may be an anhydride, a hydrate, or a solvate. When the term "salt" is simply used in the present invention, it may be in the form of anhydride, hydrate, or solvate. As for the term "anhydride" used in the present invention, it refers to the salt in a state that it is not hydrate nor solvate, and even a substance that originally does not form hydrate nor solvate is also included in the "anhydride" referred to in the present invention, so long as it does not have crystal water, hydrating water, or interacting solvent. The anhydride may also be called "anhydrate." When the salt is a hydrate, the molecular number of hydrating water is not particularly limited, and it may be monohydrate, dihydrate, or the like. Examples of the solvate include, for example, methanol solvate, ethanol solvate, propanol solvate, and 2-propanol solvate.

Particularly preferred specific examples of the salt of the present invention are the followings:
methanesulfonate of 1-(2-deoxy-2-fluoro-4-thio-β-D-arabinofuranosyl)cytosine;
hydrochloride of 1-(2-deoxy-2-fluoro-4-thio-β-arabinofuranosyl)cytosine;
½ sulfate of 1-(2-deoxy-2-fluoro-4-thio-β-D-arabinofuranosyl)cytosine;
nitrate of 1-(2-deoxy-2-fluoro-4-thio-β-D-arabinofuranosyl)cytosine; and
hydroiodide of 1-(2-deoxy-2-fluoro-4-thio-β-D-arabinofuranosyl)cytosine; as well as anhydrides of the aforementioned salts.

The salt of the present invention may be in the form of a crystal. One of the preferred embodiments of the present invention is a crystal of methanesulfonate of 1-(2-deoxy-2-fluoro-4-thio-β-D-arabinofuranosyl)cytosine showing characteristic peaks at diffraction angles (2θ) of 19.8, 21.8, 27.5, 28.4, and 29.9 degrees in powder X-ray diffractometry. Another preferred example is a crystal of hydrochloride of 1-(2-deoxy-2-fluoro-4-thio-β-D-arabinofuranosyl)cytosine showing characteristic peaks at diffraction angles (2θ) of 9.2, 14.7, 15.7, 22.9, and 27.3 degrees in powder X-ray diffractometry.

Figure 1:
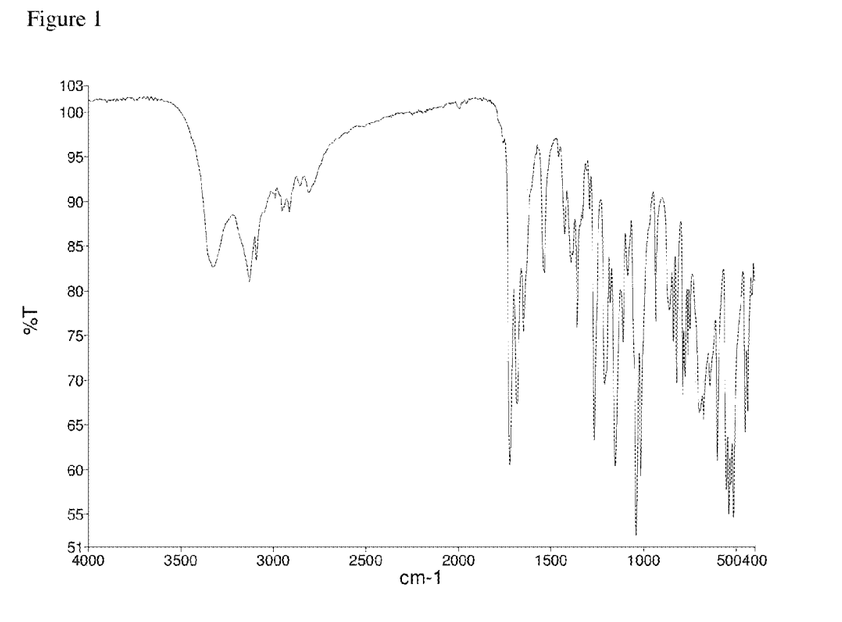
FIG. 1 shows the result of infrared absorption spectrometry of methanesulfonate of 1-(2-deoxy-2-fluoro-4-thio-β-D-arabinofuranosyl)cytosine.
Figure 2:
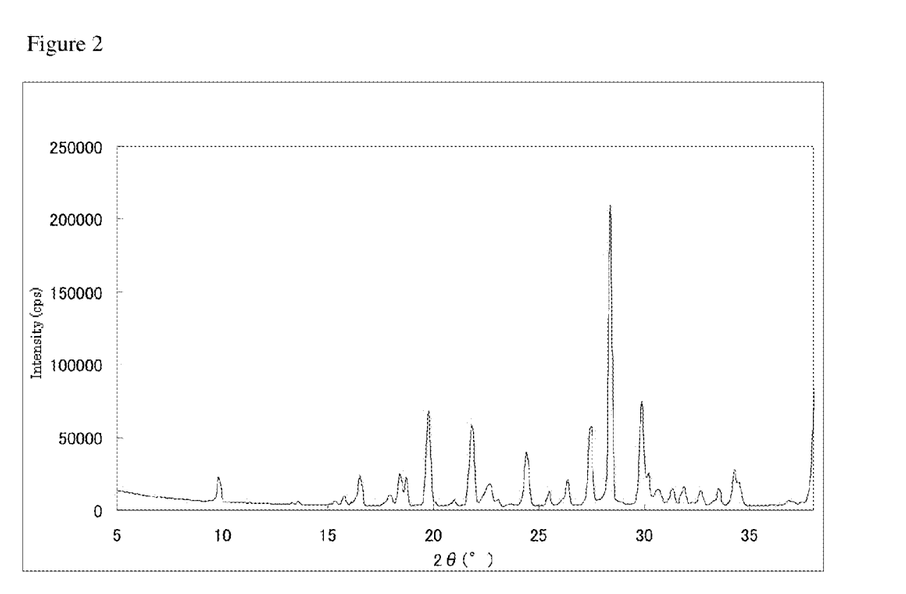
FIG. 2 shows a powder X-ray diffraction spectrum of methanesulfonate of 1-(2-deoxy-2-fluoro-4-thio-β-D-arabinofuranosyl)cytosine.

The results of the powder X-ray diffractometry of the crystal of the hydrochloride and the crystal of the methanesulfonate are shown in FIGS. 1 and 2.

Diffraction angles at which a crystal shows characteristic peaks in powder X-ray diffractometry may vary depending on the measurement conditions. In general, 2θ may include an error in the range of ±0.2 degree. Therefore, "diffraction angle of X degrees as 2θ" referred to in the present invention means a "diffraction angle of ((X−0.2) to (X+0.2)) degrees as 2θ", unless specifically indicated. Accordingly, not only a crystal showing characteristic peaks in powder X-ray diffractometry at diffraction angles completely agreeing with the defined angles, but also a crystal showing characteristic peaks at diffraction angles agreeing with the defined angles with an error in the range of ±0.2 degree falls within the scope of the present invention.

Hereafter, the method for preparing the salt of the present invention will be explained. Compound A can be prepared by the method described in Patent document 1 or Journal of Organic Chemistry, Vol. 64, pp. 7912-7920, 1999. A salt of Compound A, and a hydrate or a solvate thereof can be prepared by a combination of known methods, and they can be prepared by, for example, the following preparation methods.

A salt of Compound A can be prepared by suspending Compound A in a poor solvent, adding an acid to dissolve the compound, and then removing the solvent, or adding a solvent in which the dissolved salt of Compound A is insoluble to deposit the salt. More specifically, a salt of Compound A can be prepared by suspending Compound A in water, adding an acid to dissolve the compound, and then evaporating the water. Alternatively, a salt of Compound A can be produced by suspending Compound A in water, adding an acid to dissolve the compound, and then adding acetone to deposit the salt.

Examples of the poor solvent include, for example, water, acetone, acetonitrile, ethyl acetate, isopropyl acetate, methanol, ethanol, propanol, and 2-propanol, and these may be used as a mixture. The amount of the poor solvent to be used is 2.5- to 120-fold amount, preferably 5- to 60-fold amount, more preferably 10- to 30-fold amount, relative to Compound A (v/w). The amount of the acid to be used is, although it depends on type of the acid, 0.5 to 4.0 equivalents, preferably 1.0 to 2.0 equivalents, more preferably 1.0 to 1.5 equivalents, of Compound A.

Examples of the solvent in which the salt is insoluble include, for example, acetone, isopropyl acetate, ethanol, propanol, and 2-propanol, and these may be used as a mixture. The amount of the solvent in which the salt is insoluble to be used is 2.5- to 120-fold amount, preferably 5- to 60-fold amount, more preferably 10- to 30-fold amount, relative to Compound A (v/w).

The salt provided by the present invention shows superior solubility, physical and chemical stabilities (deliquescent property, efflorescent property, vaporization property, evaporation property, solidification property, coagulation property, change with light, change of color, decomposition, generation of insoluble matter), and manufacturability (ease of handling in manufacture), and thus it is useful as a bulk drug for medicaments.

The salt of Compound A of the present invention can be used as an antitumor agent, or an active ingredient of a pharmaceutical composition. In the present invention, the term "treatment" includes prophylactic treatment and therapeutic treatment.

The pharmaceutical composition of the present invention can be used for a treatment of a tumor. The pharmaceutical composition of the present invention can be effectively used for a treatment of tumors of various types, including melanoma, hepatoma, neuroglioma, neuroblastoma, sarcoma, tumors of lung, colon, udder, bladder, ovary, testis, prostate gland, cervical part, pancreas, stomach, small intestine, and other organs. Among various kinds of the salts of Compound A, only one kind may be used for the pharmaceutical composition of the present invention, or two or more kinds of the salts may be contained. The pharmaceutical composition of the present invention may be used in combination with other therapeutic drugs containing a known antitumor agent conventionally used in this field.

The pharmaceutical composition of the present invention may usually contain additives used for drug manufacturing, such as excipient, binder, lubricant, disintegrating agent, colorant, corrigent, emulsifier, surfactant, dissolving aid, suspending agent, isotonic agent, buffering agent, preservative, anti-oxidant, stabilizer, and absorption enhancer.

As for the administration route of the pharmaceutical composition of the present invention, examples of the administration method include, for example, intravenous, intraarterial, intrarectal, intraperitoneal, intramuscular, intratumorale and intracystic injections, oral administration, dermal administration, use of suppository, and the like. As for dose and administration frequency, for example, 0.01 to 1000 mg/kg per day of the salt of the present invention can be administered orally or parenterally (for example, injection, drip infusion, administration to rectal part, etc.) to an adult once a day, or several times a day with dividing the foregoing dose. Examples of the form of the pharmaceutical composition as a pharmaceutical preparation include tablet, capsule, powder, syrup, granule, pill, suspension, emulsion, solution, powdery preparation, suppository, eye drop, nose drop, ear drop, patch, ointment, and injection.

EXAMPLES

In order to clarify usefulness of the compound of the present invention, the present invention will be explained with reference to the following test examples.

Test Example 1: Antitumor Activity

The compounds of Examples 1 and 2 were chosen as test compounds.

Compound A was chosen as a comparative compound.

Cells at the logarithmic phase were inoculated on a 96-well plate at a density of 1000 cells/well (BxPC-3, MIA PaCa-2) or 3000 cells/well (Capan-1), and cultured overnight at 37° C. in a $CO_2$ incubator. On the next day, serially diluted solutions of each test compound were added, and culture was performed for 3 days in an incubator. After completion of the culture, by using a cell proliferation assay kit ATPlite (Perkin Elmer), and a plate reader Envision (Perkin Elmer), emission was measured. Concentrations of the test compounds providing 50% of cell proliferation inhibition ($IC_{50}$) were calculated by fitting using a sigmoid function. The solutions of the test compounds were prepared by diluting them with PBS (pH 7.4) at 10 mM, and further diluting the 10 mM solutions with PBS (pH 7.4), and used in the test.

The results are shown in Table 1.

TABLE 1

| Test compound | $IC_{50}$ (nM) | | |
| --- | --- | --- | --- |
| | BxPC-3 | Capan-1 | MIA PaCa-2 |
| Example 1 (methanesulfonate) | 45 | 36 | 373 |
| Example 2 (hydrochloride) | 41 | 31 | 417 |
| Comparative compound | 45 | 35 | 382 |

The compounds of the present invention showed superior antitumor activity.

Test Example 2: Solubility Test

The compounds of Examples 1 to 5 were chosen as test compounds.

Compound A was chosen as a comparative compound.

Each of the test compounds and the comparative compound was added to water, and the mixture was stirred at room temperature for 24 hours. The insoluble matter was removed by filtration using a membrane filter (0.2 μm). The filtrate was analyzed by high performance liquid chromatography (HPLC) to obtain the solubility.

The results are shown in Table 2.

TABLE 2

| Test compound | Solubility in water (mg/mL) |
| --- | --- |
| Example 1 (methanesulfonate) | 79 |
| Example 2 (hydrochloride) | 67 |
| Example 3 (½ sulfate) | 35 |
| Example 4 (nitrate) | 45 |
| Example 5 (hydroiodide) | 128 |
| Comparative compound | 2 |

The compounds of the present invention showed high solubility in water, i.e., superior solubility.

Test Example 3: Stability Test

The compounds of Examples 1 and 2 were chosen as test compounds.

The compounds of Examples 1 and 2 were stored for 2 weeks in an open state under conditions of 60° C. and 75% relative humidity. The test compounds were macroscopically observed after the storage, and presence or absence of deliquescence was examined. As a result, the compounds of Examples 1 and 2 did not deliquesce, but were stable.

The compounds of the present invention did not show deliquescent property, but showed superior stability.

Test Example 4: Flowability Test

The compounds of Examples 1 and 2 were chosen as test compounds.

Compound A was chosen as a comparative compound.

Each of the test compounds and the comparative compound was sieved with 177 μm (80M) mesh to obtain a powdery sample. The obtained powdery sample was roughly filled in a glass measuring cylinder (10 $cm^3$), the upper surface of the powder layer was horizontally smoothened, and the value of the volume was read. The weight of the powdery sample was divided with the volume to obtain loose bulk density (g/cm$^3$).

Then, the glass measuring cylinder filled with the powdery sample was tapped by using a general powdery characteristic measuring apparatus (Powdertester Type PT-E, Hosokawa Micron CORP.). When the volume of the powder layer no longer changed, the value of the volume was read. The weight of the powdery sample was divided with the volume to obtain compacted bulk density (g/cm$^3$).

The compaction rate (%) was obtained in accordance with the following equation.

Compaction rate (%)=[(Compacted bulk density−Loose bulk density)/Compacted bulk density]×100

The results are shown in Table 3.

TABLE 3

| Test compound | Compaction rate (%) |
| --- | --- |
| Example 1 (methanesulfonate) | 18 |
| Example 2 (hydrochloride) | 21 |
| Comparative compound | 41 |

The compounds of the present invention showed small compaction rates, and thus showed superior flowability. The compounds of the present invention showed superior physical properties.

Test Example 5: Tableting Property Test

The compounds of Examples 1 and 2 were chosen as test compounds.

Compound A was chosen as a comparative compound.

Each of the test compounds and the comparative compound was sieved with 177 μm (80M) mesh to obtain a powdery sample. The obtained powdery sample was compression-molded by using a tableting machine (Tableting Machine HT-P18A, Hata Iron Works, Ltd.; tableting diameter, 6.5 mm; tableting pressure, 1000 kgf; tablet weight, 100 mg) to obtain tablets. The obtained tablets were macroscopically observed, and graded according to the following criteria.
5 Points: Surface has gloss.
4 Points: Surface is slightly roughened.
3 Points: Surface is roughened.
2 Points: Surface is slightly chipped.
1 Point: Surface is chipped.
0 Point: Tablets stick to pestle, and cannot be unstuck.

The tableting was performed five times, and averages of the scores of the tablets were calculated. The results are shown in Table 4.

TABLE 4

| Test compound | Score |
| --- | --- |
| Example 1 (methanesulfonate) | 4.5 |
| Example 2 (hydrochloride) | 5.0 |
| Comparative compound | 1.0 |

The compounds of the present invention showed high scores, and thus showed superior tableting property. The compounds of the present invention showed superior physical properties.

Hereafter, the present invention will be explained with reference to examples. However, the present invention is not limited to these examples.

Moisture content was measured with a Karl Fischer moisture meter.

Infrared absorption spectrum was measured by the infrared absorption attenuated total reflectance spectroscopy (ATR method).

In the examples, the abbreviations have the following meanings.
Compound A: 1-(2-Deoxy-2-fluoro-4-thio-β-D-arabinofuranosyl)cytosine
DMSO-D$_6$: Heavy dimethyl sulfoxide Example 1

Compound A was prepared according to the method described in Journal of Organic Chemistry, Vol. 64, pp. 7912-7920, 1999 (the same shall apply to the following examples). Methanesulfonic acid (0.99 mL) was added to a suspension of Compound A (4.0 g) in water (73 mL), and the mixture was stirred at room temperature for 35 minutes. After dissolution was visually confirmed, the solvent was evaporated under reduced pressure. Acetone (75 mL) was added to the obtained residue, and the mixture was stirred at room temperature for 30 minutes. The solid matter was collected by filtration, washed with acetone, and air-dried to obtain methanesulfonate of Compound A (5.2 g) as a white solid. Moisture content: 1.3% (weight ratio).
$^1$H-NMR (DMSO-D$_6$) δ: 9.55 (1H, s), 8.56 (1H, s), 8.46 (1H, d, J=7.9 Hz), 6.28 (1H, dd, J=10.6, 5.3 Hz), 6.14 (1H, d, J=7.9 Hz), 5.06 (1H, dt, J=50.2, 5.9 Hz), 4.24-4.13 (1H, m), 3.80-3.61 (2H, m), 3.23 (1H, q, J=5.7 Hz), 2.35 (3H, s)

The result of infrared absorption spectrometry of the obtained crystal of the methanesulfonate of Compound A is shown in FIG. 1.

Powder X-ray diffraction of the obtained crystal of the methanesulfonate of Compound A was measured.
Conditions of powder X-ray diffractometry:
X-ray used: CuKα
Applied voltage: 50 kV
Applied current: 280 mA
Scanning axis: 2θ

The obtained powder X-ray diffraction spectrum is shown in FIG. 2 and Table 5.

TABLE 5

| 2θ | d (Å) | Relative intensity (%) |
| --- | --- | --- |
| 16.514 | 5.368 | 9 |
| 18.431 | 4.814 | 10 |
| 18.699 | 4.746 | 9 |
| 19.770 | 4.491 | 31 |
| 21.817 | 4.074 | 27 |
| 24.428 | 3.644 | 17 |
| 27.455 | 3.249 | 26 |
| 28.388 | 3.144 | 100 |
| 29.895 | 2.989 | 33 |
| 34.322 | 2.613 | 12 |

Example 2

Concentrated hydrochloric acid (1.31 mL) was added to a suspension of Compound A (4.0 g) in water (68 mL), and the mixture was stirred at room temperature for 1 hour. After dissolution was visually confirmed, the solvent was evaporated under reduced pressure. Acetone (68 mL) was added to the obtained residue, and the mixture was stirred at room temperature for 1 hour. The solid matter was collected by filtration, washed with acetone, and air-dried to obtain hydrochloride of Compound A (4.5 g) as a white solid. Moisture content: 0.9% (weight ratio).

$^1$H-NMR (DMSO-D$_6$) δ: 9.80 (1H, s), 8.71 (1H, s), 8.47 (1H, d, J=7.9 Hz), 6.27 (1H, dd, J=9.9, 5.3 Hz), 6.21 (1H, d, J=7.9 Hz), 5.07 (1H, dt, J=50.4, 6.1 Hz), 4.22-4.14 (1H, m), 3.80-3.61 (2H, m), 3.23 (1H, q, J=5.7 Hz)

Figure 3:
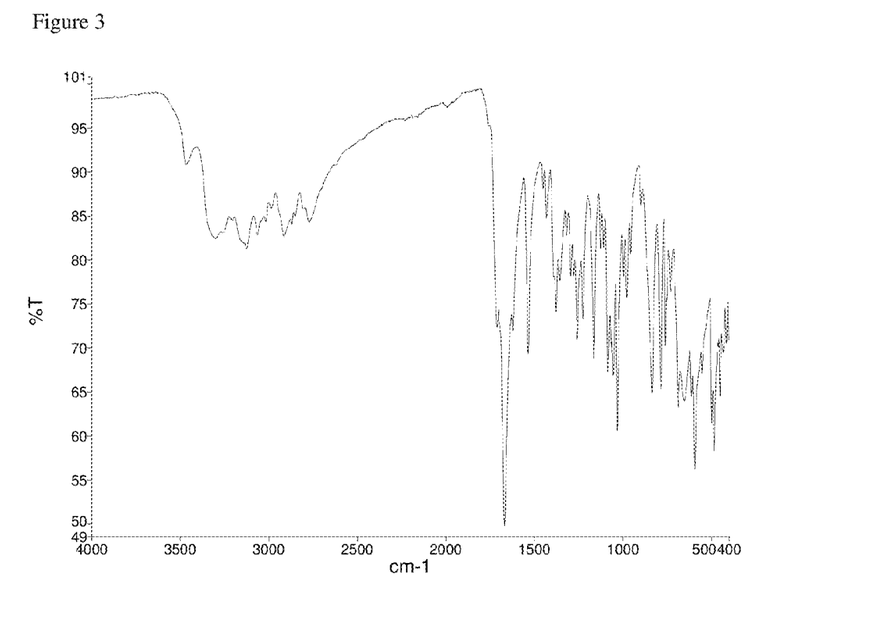
FIG. 3 shows the result of infrared absorption spectrometry of hydrochloride of 1-(2-deoxy-2-fluoro-4-thio-β-D-arabinofuranosyl)cytosine.

The result of infrared absorption spectrometry of the obtained crystal of the hydrochloride of Compound A is shown in FIG. 3.

Figure 4:
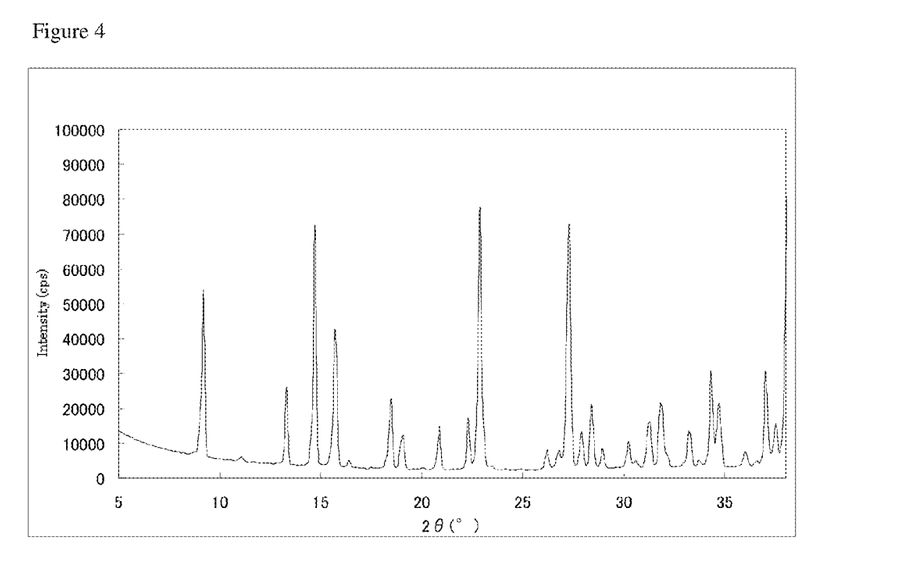
FIG. 4 shows a powder X-ray diffraction spectrum of hydrochloride of 1-(2-deoxy-2-fluoro-4-thio-β-D-arabinofuranosyl)cytosine.

Powder X-ray diffraction of the obtained crystal of the hydrochloride of Compound A was measured. The measurement conditions were the same as those used in Example 1. The obtained powder X-ray diffraction spectrum is shown in FIG. 4 and Table 6.

TABLE 6

| 2θ | d (Å) | Relative intensity (%) |
|---|---|---|
| 9.172 | 9.642 | 64 |
| 13.299 | 6.658 | 30 |
| 14.704 | 6.025 | 92 |
| 15.713 | 5.640 | 53 |
| 18.458 | 4.807 | 26 |
| 22.879 | 3.887 | 100 |
| 27.261 | 3.271 | 86 |
| 34.336 | 2.612 | 34 |
| 34.677 | 2.587 | 23 |
| 37.031 | 2.428 | 34 |

Example 3

Sulfuric acid (5 μL) was added to a suspension of Compound A (50 mg) in water (1.0 mL), and the mixture was stirred at room temperature for 10 minutes. After dissolution was visually confirmed, the solvent was evaporated under reduced pressure. Acetone (1.0 mL) was added to the obtained residue. The solid matter was collected by filtration, and air-dried to obtain ½ sulfate of Compound A (50 mg) as a white solid.

$^1$H-NMR (D$_2$O) δ: 8.56 (1H, d, J=8.6 Hz), 6.40 (1H, dd, J=8.9, 5.6 Hz), 6.26 (1H, d, J=7.9 Hz), 5.19 (1H, dt, J=50.0, 6.3 Hz), 4.42-4.34 (1H, m), 3.94-3.84 (2H, m), 3.44 (1H, q, J=5.5 Hz)

Example 4

60% Nitric acid (0.014 mL) was added to a suspension of Compound A (50 mg) in water (1.0 mL), and the mixture was stirred at room temperature for 10 minutes. After dissolution was visually confirmed, the solvent was evaporated under reduced pressure. Acetone (1.0 mL) was added to the obtained residue. The solid matter was collected by filtration, and air-dried to obtain nitrate of Compound A (70 mg) as a white solid.

$^1$H-NMR (DMSO-D$_6$) δ: 9.50 (1H, s), 8.45 (1H, d, J=7.9 Hz), 8.35 (1H, s), 6.29 (1H, dd, J=10.6, 5.3 Hz), 6.13 (1H, d, J=7.9 Hz), 5.06 (1H, dt, J=50.2, 5.9 Hz), 4.22-4.14 (1H, m), 3.71 (2H, m), 3.24 (1H, q, J=5.6 Hz)

Example 5

57% Hydroiodic acid (0.025 mL) was added to a suspension of Compound A (50 mg) in water (1.0 mL), and the mixture was stirred at room temperature for 10 minutes. After dissolution was visually confirmed, the solvent was evaporated under reduced pressure. Acetone (1.0 mL) was added to the obtained residue. The solid matter was collected by filtration, and air-dried to obtain hydroiodide of Compound A (50 mg) as a white solid.

$^1$H-NMR (DMSO-D$_6$) δ: 9.51 (1H, s), 8.45 (1H, d, J=7.9 Hz), 8.38 (1H, s), 6.29 (1H, dd, J=10.6, 5.3 Hz), 6.13 (1H, d, J=7.9 Hz), 5.06 (1H, dt, J=50.2, 5.9 Hz), 4.22-4.14 (1H, m), 3.71 (2H, m), 3.24 (1H, q, J=5.6 Hz)

INDUSTRIAL APPLICABILITY

The salt of the present invention shows at least one or more of such characteristics as (1) it has superior antitumor activity, (2) it shows superior crystallinity, (3) it shows high water solubility, (4) it does not show deliquescent property, (5) it shows superior flowability, (6) it shows superior tableting property, (7) it can be manufactured with less environmental load, and (8) it can be manufactured in a large scale, and therefore it is useful as a bulk drug for medicaments.

The invention claimed is:

1. A crystal of methanesulfonate of 1-(2-deoxy-2-fluoro-4-thio-β-D-arabinofuranosyl)cytosine showing characteristic peaks at diffraction angles (2θ) of 19.8, 21.8, 27.5, 28.4, and 29.9 degrees in powder X-ray diffractometry.

2. A pharmaceutical composition containing the crystal according to claim 1 and a pharmaceutically acceptable additive.

3. The pharmaceutical composition according to claim 2, which is for use in a treatment of a tumor.

4. A method for preparing the crystal according to claim 1, which comprises the step of converting 1-(2-deoxy-2-fluoro-4-thio-β-D-arabinofuranosyl)cytosine into the methanesulfonate thereof and crystallizing said salt.

5. A method for treating a tumor in a subject comprising the step of administering to a subject in need of such treatment the crystal according to claim 1.

6. A crystal of hydrochloride of 1-(2-deoxy-2-fluoro-4-thio-β-D-arabinofuranosyl)cytosine showing characteristic peaks at diffraction angles (2θ) of 9.2, 14.7, 15.7, 22.9, and 27.3 degrees in powder X-ray diffractometry.

7. A pharmaceutical composition containing the crystal according to claim 6 and a pharmaceutically acceptable additive.

8. The pharmaceutical composition according to claim 6, which is for use in a treatment of a tumor.

9. A method for preparing the crystal according to claim 6, which comprises the step of converting 1-(2-deoxy-2-fluoro-4-thio-β-D-arabinofuranosyl)cytosine into the hydrochloride thereof and crystallizing said salt.

10. A method for treating a tumor in a subject comprising the step of administering to a subject in need of such treatment the crystal according to claim 6.

* * * * *